United States Patent
Bienkiewicz

(10) Patent No.: US 8,993,514 B1
(45) Date of Patent: Mar. 31, 2015

(54) PRION PROTEIN BASED HEMIN BINDERS AND METHODS OF USE

(71) Applicant: The Florida State University Research Foundation, Inc., Tallahassee, FL (US)

(72) Inventor: Ewa Bienkiewicz, Tallahassee, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 0 days.

(21) Appl. No.: 13/936,373

(22) Filed: Jul. 8, 2013

Related U.S. Application Data

(63) Continuation-in-part of application No. 13/446,205, filed on Apr. 13, 2012, now Pat. No. 8,481,482.

(60) Provisional application No. 61/474,790, filed on Apr. 13, 2011.

(51) Int. Cl.
  *A61K 38/16* (2006.01)
  *A61K 38/17* (2006.01)
  *A61K 38/10* (2006.01)

(52) U.S. Cl.
  CPC .............. *A61K 38/1709* (2013.01); *A61K 38/10* (2013.01)
  USPC ......................................................... 514/2.1

(58) Field of Classification Search
  None
  See application file for complete search history.

(56) References Cited

U.S. PATENT DOCUMENTS 8,481,482 B1 * 7/2013 Bienkiewicz .................. 514/1.1

OTHER PUBLICATIONS

Lee et al (Journal of Biological Chemistry (Dec. 14, 2007) 282(50): 36525-36533).*
Liu et al., Loss of vascular early response gene reduces edema formation after experimental stroke, Experimental & Translational Stroke Medicine, 2012, 4:12.
Robinson et al., Hemin toxicity: a preventable source of brain damage following hemorrhagic stroke, Redox Report, 2009, vol. 14, No. 6.
Lee et al., Hemin Interactions and Alterations of the Subcellular Localization of Prion Protein, Journal of Biological Chemistry, Dec. 14, 2007, vol. 282, No. 50.
Belayev et al., Experimental intracerebral hematoma in the rat: Characterization by sequential magnetic resonance imaging, behavior, and histopathology. Effect of albumin therapy, Brain Research 1157, 2007, 146-155.

* cited by examiner

*Primary Examiner* — Karlheinz R Skowronek
*Assistant Examiner* — Mindy Newman
(74) *Attorney, Agent, or Firm* — Christopher M. Ramsey; GrayRobinson, P.A.

(57) ABSTRACT

Methods of using portions of the N-terminal domain of prion protein for binding hemin are disclosed. In a particular embodiment, a method comprises administering at least one isolated amino acid sequence comprising a peptide from the octarepeat region of $PrP^C$ to a solution containing hemin, wherein the isolated amino acid sequence is effective for forming one or more chemical bonds with hemin.

23 Claims, 12 Drawing Sheets

SEQUENCE LISTING

```
<160> NUMBER OF SEQ ID NOS: 6

<210> SEQ ID NO 1
<211> LENGTH: 253
<212> TYPE: PRT
<213> ORGANISM: Homo sapiens

<400> SEQUENCE: 1

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Gly Trp Gly Gln Pro His Gly Gly Gly
    50                  55                  60

Trp Gly Gln Pro His Gly Gly Gly Trp Gly Gln Pro His Gly Gly Gly
65                  70                  75                  80

Trp Gly Gln Pro His Gly Gly Gly Trp Gly Gln Gly Gly Gly Thr His
                85                  90                  95

Ser Gln Trp Asn Lys Pro Ser Lys Pro Lys Thr Asn Met Lys His Met
            100                 105                 110

Ala Gly Ala Ala Ala Ala Gly Ala Val Val Gly Gly Leu Gly Gly Tyr
        115                 120                 125
```

```
Met Leu Gly Ser Ala Met Ser Arg Pro Ile Ile His Phe Gly Ser Asp
        130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Glu Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Ile Thr Gln Tyr Glu Arg Glu Ser Gln Ala
        210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250

<210> SEQ ID NO 2
<211> LENGTH: 8
<212> TYPE: PRT
<213> ORGANISM: Artificial Sequence
<220> FEATURE:
<223> OTHER INFORMATION: SYNTHETICALLY GENERATED PEPTIDE

<400> SEQUENCE: 2

Pro His Gly Gly Gly Trp Gly Gln
1               5

<210> SEQ ID NO 3
<211> LENGTH: 16
<212> TYPE: PRT
<213> ORGANISM: Artificial Sequence
<220> FEATURE:
<223> OTHER INFORMATION: SYNTHETICALLY GENERATED PEPTIDE

<400> SEQUENCE: 3

Pro His Gly Gly Gly Trp Gly Gln Pro His Gly Gly Gly Trp Gly Gln
1               5                   10                  15

<210> SEQ ID NO 4
<211> LENGTH: 24
<212> TYPE: PRT
<213> ORGANISM: Artificial Sequence
<220> FEATURE:
<223> OTHER INFORMATION: SYNTHETICALLY GENERATED PEPTIDE

<400> SEQUENCE: 4

Pro His Gly Gly Gly Trp Gly Gln Pro His Gly Gly Gly Trp Gly Gln
1               5                   10                  15

Pro His Gly Gly Gly Trp Gly Gln
            20

<210> SEQ ID NO 5
<211> LENGTH: 32
<212> TYPE: PRT
<213> ORGANISM: Artificial Sequence
<220> FEATURE:
<223> OTHER INFORMATION: SYNTHETICALLY GENERATED PEPTIDE
```

```
<400> SEQUENCE: 5

Pro His Gly Gly Gly Trp Gly Gln Pro His Gly Gly Gly Trp Gly Gln
1               5                   10                  15

Pro His Gly Gly Gly Trp Gly Gln Pro His Gly Gly Gly Trp Gly Gln
                20                  25                  30

<210> SEQ ID NO 6
<211> LENGTH: 37
<212> TYPE: PRT
<213> ORGANISM: Artificial Sequence
<220> FEATURE:
<223> OTHER INFORMATION: Synthetically generated peptide

<400> SEQUENCE: 6

Gly Gln Pro His Gly Gly Gly Trp Gly Gln Pro His Gly Gly Gly Trp
1               5                   10                  15

Gly Gln Pro His Gly Gly Gly Trp Gly Gln Pro His Gly Gly Gly Trp
                20                  25                  30

Gly Gln Gly Gly Gly
                35
```

PRION PROTEIN BASED HEMIN BINDERS AND METHODS OF USE

CROSS REFERENCE TO RELATED APPLICATIONS

This is a continuation-in-part of application Ser. No. 13/446,205, titled "Prion Protein Based Hemin Binders and Methods of Use, filed on Apr. 13, 2012, now U.S. Pat. No. 8,481,482, which claimed the benefit of provisional application Ser. No. 61/474,790 titled "Therapeutic Agent Targeting Hemin and Related Methods," filed on Apr. 13, 2011. Each of these applications is incorporated by reference in its entirety.

FIELD OF THE INVENTION

This invention relates to the field of peptide-hemin interactions and, more particularly, to methods of using amino acid sequences found in prion protein to bind hemin.

SEQUENCE LISTING

This application contains a Sequence Listing electronically submitted via EFS-web to the United States Patent and Trademark Office as a text file named "Sequence_Listing.txt." The electronically filed Sequence Listing serves as both the paper copy required by 37 C.F.R. §1.821(c) and the computer readable file required by 37 C.F.R. §1.821(c). The information contained in the Sequence Listing is incorporated herein by reference in its entirety.

BACKGROUND

The prion protein, PrP for short, is found throughout the body of humans and other animals. PrP exists in two forms. The normal endogenous form of PrP, called $PrP^C$ or cellular PrP, is non-infectious. In contrast, the second form of PrP, called $PrP^{SC}$, is infectious. The difference is primarily attributable to the fact that the molecular structure of $PrP^{SC}$ is mis-folded relative to that of $PrP^C$.

$PrP^{SC}$ is responsible for causing prion diseases, including transmissible spongiform encephalopathies such as mad cow disease and Creutzfeldt-Jakob disease. $PrP^{SC}$ is also responsible for generating amyloid fibrils in neural tissue, which can result in irreversible neurodegeneration.

$PrP^C$, on the other hand, appears to be involved in numerous cellular functions, including signal transduction, neuroprotection, and angiogenesis.

Heme is an iron containing component of hemoproteins such as hemoglobin and is an essential component of oxygen transport. Hemin, a derivative of heme, is produced by the body and is released in a vascular injury event such as a stroke.

Hemin toxicity is a source of brain damage following hemorrhagic stroke. Hemorrhagic stroke involves the rupture of an intracerebral artery, which subsequently results in a hematoma caused by the pooling of blood. This prevents the cells from receiving oxygen and vital nutrients, causing the cells to die. After the acute brain injury caused by the stroke, brain damage can continue to occur over the following days and weeks. This has been attributed to the presence of hemin at the site of the hematoma (Robinson, et al, "Hemin toxicity: a preventable source of brain damage following hemorrhagic stroke." *Redox Report*, Vol. 14, No. 6 (2009)). According to Robinson, et al., elevated levels of hemin can be toxic, causing tissue injury and even death. Blood contains about 2.5 mM of hemoglobin, which, when broken down can yield 10 mM of hemin. Cell culture experiments suggest that as little as 3-30 µM of hemin is sufficient to kill 60%-70% of cultured neurons and astrocytes within 4-14 hours.

SUMMARY

In view of the foregoing, it is an object of the invention is to provide methods of using portions of the N-terminal domain of $PrP^C$ to bind hemin. Advantageously, the methods may prevent injury to tissue or cells caused by cellularly toxic hemin levels.

In one embodiment, a method of treating a condition characterized by cellularly toxic hemin levels, comprises administering a composition comprising an isolated amino acid sequence selected from the group consisting of SEQ ID NOs: 2, 3, 4, 5, 6, and combinations thereof to a subject identified as having the condition.

In another embodiment, a method of treating a condition characterized by cellularly toxic hemin levels, comprises administering a composition comprising at least one isolated amino acid sequence consisting essentially of SEQ ID NO: 2, 3, 4, 5, or 6 to a subject identified as having the condition.

In another embodiment, a method of binding hemin comprises administering a composition comprising at least one isolated amino acid sequence selected from SEQ ID NO: 2, 3, 4, 5, or 6 to a solution containing hemin, wherein the isolated amino acid sequence is effective for forming one or more chemical bonds with hemin.

In some embodiments, the isolated amino acid sequence consists of SEQ ID NO: 2, 3, 4, 5, or 6. In others, the composition comprises a combination of the isolated amino acid sequences and at least one of the isolated amino acid sequences in the composition consists of SEQ ID NO: 2, 3, 4, 5, or 6.

In some embodiments, the N-terminus of the isolated amino acid sequence is acetylated and the C-terminus of the isolated amino acid sequence is amidated.

In some embodiments, the composition is administered when the solution containing hemin has a pH below 7.4.

These and other objects, aspects, and advantages of the present invention will be better appreciated in view of the drawings and following detailed description of the preferred embodiments.

DETAILED DESCRIPTION OF PREFERRED EMBODIMENTS

In the Summary above and in the Detailed Description of Preferred Embodiments, reference is made to particular features (including method steps) of the invention. It is to be understood that the disclosure of the invention in this specification includes all possible combinations of such particular features. For example, where a particular feature is disclosed in the context of a particular aspect or embodiment of the invention, that feature can also be used, to the extent possible, in combination with and/or in the context of other particular aspects and embodiments of the invention, and in the invention generally.

The term "comprises" is used herein to mean that other features, ingredients, steps, etc. are optionally present. When reference is made herein to a method comprising two or more defined steps, the steps can be carried in any order or simultaneously (except where the context excludes that possibility), and the method can include one or more steps which are carried out before any of the defined steps, between two of the defined steps, or after all of the defined steps (except where the context excludes that possibility).

This invention may be embodied in many different forms and should not be construed as limited to the embodiments set forth herein. Rather, these embodiments are provided so that this disclosure will be thorough and complete, and will convey preferred embodiments of the invention to those skilled in the art.

As used herein, the following terms have the following meanings. Both the singular and plural forms of a term are included, regardless of the form discussed in this section.

"Prion," prion protein," and "PrP" are used interchangeably to refer to both the pathogenic prion protein form ("PrP$^{SC}$") and the non-pathogenic prion protein form ("PrP$^C$"). Use of "prion," prion protein," and "PrP" is not meant to be limited to the polypeptides having the exact sequences as those described herein.

"PrP$^C$" means the native prion protein, which is naturally expressed in Mammallia.

"PrP$^{SC}$" means the structurally altered form of PrP$^C$ that is considered to be pathogenic.

"Ischemic stroke" means a stroke caused by blockage of blood supply. Typical blockages are caused by a thrombus or embolus.

"Hemmorrhagic stroke" means a stroke involving the rupture of an artery and subsequent hematoma.

Figure 1:
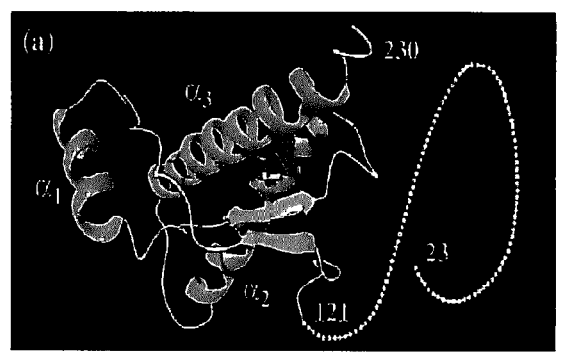
FIG. 1 is a diagram of the molecular structure of $PrP^C$ from residues 23-230 as determined by NMR data.

FIG. 1 is a diagram of the structure of PrP$^C$ from residues 23-231. It includes a plurality of α-helix regions and β pleated-sheet regions. The C-terminal domain is structurally ordered while the N-terminal domain is referred to as being "flexibly disordered." To provide a better understanding of aspects of the invention, this structure has been simplified into the simple schematic of FIG. 2. The portion of the sequence beginning with residue 23 is called the N-terminal domain. The opposite end is called the C-terminal domain. The relative locations of the α-helix regions and β pleated-sheet regions are indicated, respectively, by the α and β symbols.

The human amino acid sequence of a full length human PrP$^C$ is provided in TABLE 1. A section of the sequence called the "ocatarepeat region" or "OR region" is bolded.

TABLE 1

Amino acid sequence of human PrP$^c$

| SEQ ID NO: | Sequence |
|---|---|
| 1 | MANLGCWMLVLFVATWSDLGLCKKRPKPGGWNTGGSRYPGQGSPG GNRYPPQGGGWGQPHGGGWGQPHGGGWGQPHGGGWGQPHGGGWG QGGTHSQWNKPSKPKTNMKHMAGAAAAGAVVGGLGGYMLGSAMSR PIIHFGSDYEDRYYRENMHRYPNQVYYRPMDEYSNQNNFVHDCVN ITIKQHTVTTTTKGENFTETDVKMMERVVEQMCITQYERESQAYY QRGSSMVLFSSPPVILLISFLIFLIVG |

Figure 2:
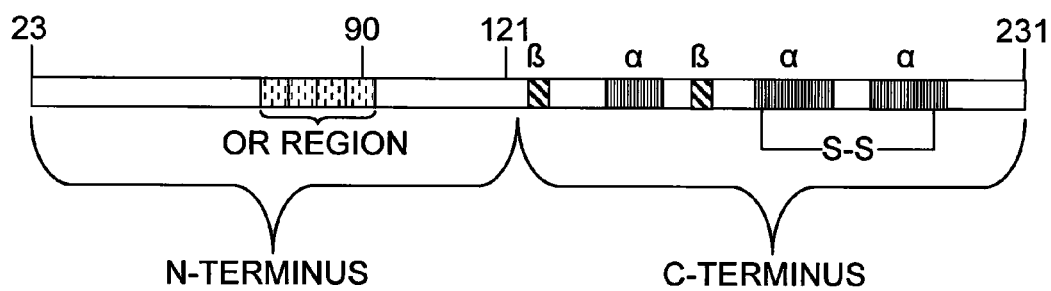
FIG. 2 is a schematic of the structure of $PrP^C$, highlighting certain features of the structure.

The octarepeat region contains a sequence of eight amino acid residues, an octamer, that repeats four times. The location of the OR region in the N-terminal domain is indicated in FIG. 2. TABLE 2 provides the amino acid sequences corresponding to 1, 2, 3, and 4 repeats and their corresponding SEQ ID NOs. SEQ ID NO: 5, includes the 4-repeat fragment of SEQ ID NO: 4, but also includes the underlined residues. When isolated, SEQ ID NOs: 2-6 adopt a modular structure.

TABLE 2

Amino acid sequences of the 1-, 2-, 3-, and 4-repeat peptides of the octarepeat region

| #Repeats | SEQ ID NO: | Sequence |
|---|---|---|
| 1 | 2 | PHGGGWGQ |
| 2 | 3 | PHGGGWGQPHGGGWGQ |
| 3 | 4 | PHGGGWGQPHGGGWGQPHGGGWGQ |
| 4 | 5 | PHGGGWGQPHGGGWGQPHGGGWGQPHGGGWGQ |
| 4 | 6 | GQPHGGGWGQPHGGGWGQPHGGGWGQPHGGGWGQGGG |

Figure 3:
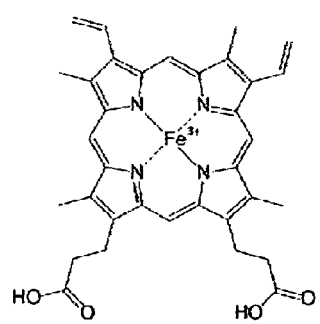
FIG. 3 is a diagram of a hemin molecule.

The inventor has found that isolated portions of the N-terminal domain chemically bind to hemin molecules, thereby presenting a therapeutic agent for preventing vascular injury caused by hemin after a vascular injury causing event. In particular, isolated fragments of the N-terminal domain that include SEQ ID NOs: 2, 3, 4, 5, 6 or combinations thereof are particularly effective for binding hemin. The structure of hemin is shown in FIG. 3. Hemin is a Fe(3+) containing porphyrin molecule in which the Fe(3+) ion is coordinated to the four N atoms of the porphyrin ligand.

The invention advantageously provides methods preventing or treating the toxic effects of hemin to vascular and neural tissue, which occur as a result of a condition involving cellularly toxic hemin levels, such as a hemorrhagic stroke or ischemic stroke, or traumatic brain injury (TBI) for example.

In these embodiments, isolated amino acid sequences of SEQ ID NOs: 2-6, fragments thereof, variants thereof, or homologues thereof may be used to bind hemin. Embodiments of the invention are intended to include one or more combinations of SEQ ID NOs: 2-6, one or more combinations of fragments thereof, one or more combinations of variants thereof, and one or more combinations of homologues thereof. The term "isolated" in this case, means that the specified amino acid sequence, fragment, variant, or homologue is present separately from the native PrP$^C$ protein.

A fragment is an amino acid sequence which has at least 40%, more preferably at least 50%, more preferably at least 60%, more preferably at least 70%, more preferably at least 80%, more preferably at least 90%, more preferably at least 95% of SEQ ID NOs: 2, 3, 4, 5, or 6.

A variant is an amino acid sequence having at least 60%, more preferably at least 70%, more preferably at least 80%, more preferably at least 90%, more preferably 95% homology to SEQ ID NOs: 2, 3, 4, 5, or 6. A variant may also be an amino acid sequence having at least 60%, more preferably at least 70%, more preferably at least 80%, more preferably at least 90%, more preferably 95% positive amino acid matches compared to a sequence SEQ ID NOs: SEQ ID NOs: 2, 3, 4, 5, or 6. A positive amino acid match is defined herein as an identity or similarity defined by physical and/or chemical properties of the amino acids having the same position in two compared sequences. The homology of the sequences may be calculated using conventional algorithms.

A homologue is an amino acid sequence which has less than 60% but more than 30%, such as 50-59%, for example 55%, such as 40-49%, for example 45%, such as 30-39%, for example 35% homology to a sequence comprising SEQ ID NOs: SEQ ID NOs: 2, 3, 4, 5, or 6.

According to a first embodiment of the invention, a method of treating a condition characterized by cellularly toxic hemin levels comprises administering a composition comprising an isolated amino acid sequence selected from the group consisting of SEQ ID NOs: 2, 3, 4, 5, 6, and combinations thereof to a subject identified as having the condition.

Exemplary conditions involving cellularly toxic hemin levels include vascular injury conditions such as hemorrhagic stroke, ischemic stroke, traumatic brain injury or other traumatic injury, bleeding wounds, reperfusion, hemophilia, and sickle cell anemia. A cellularly toxic hemin level is a concentration of hemin that is sufficient to kill the cells to which hemin is administered. In a particular embodiment, the cellularly toxic hemin level is about 3 µM to about 30 µM of hemin.

Aside from the one or more isolated amino acid sequences, the composition may further comprise one or ingredients useful for making the composition into a pharmaceutically acceptable dosage form such as a suspension, tablet, capsule, injectable, or the like that can be administered to a human or animal patient. Exemplary ingredients include one or more excipients, diluents, disintegrants, emulsifiers, solvents, processing aids, buffering agents, colorants, flavorings, solvents, coating agents, binders, carriers, glidants, lubricants, granulating agents, gelling agents, polishing agents, suspending agent, sweetening agent, anti-adherents, preservatives, emulsifiers, antioxidants, plasticizers, surfactants, viscosity agents, enteric agents, wetting agents, thickening agents, stabilizing agents, solubilizing agents, bioadhesives, film forming agents, emollients, dissolution enhancers, dispersing agents, or combinations thereof.

The composition may be administered to a subject identified as having the condition characterized by cellularly toxic hemin levels by way of, for example, contacting the subject with the composition, injecting the subject with the composition, ingesting the composition, or the like. Subjects include, but are not limited to humans, animals, cells, and solutions containing hemin, including in vitro and in vivo solutions.

According to another embodiment of the invention, a method of treating a condition characterized by cellularly toxic hemin levels comprises administering a composition comprising at least one isolated amino acid sequence consisting essentially of SEQ ID NO: 2, 3, 4, 5, or 6 to a subject identified as having the condition.

The phrase "at least one isolated amino acid sequence consisting essentially of SEQ ID NO: 2, 3, 4, 5, or 6" means that at least one, but perhaps more, of the amino acid sequences consisting essentially of SEQ ID NO: 2, 3, 4, 5, or 6 may be administered. The amino acid sequence consists essentially of SEQ ID NO: 2, 3, 4, 5, or 6 when the specific form of the sequence does not materially change the ability of the sequence to bind with hemin.

According to another embodiment of the invention, a method of binding hemin comprises administering a composition comprising at least one isolated amino acid sequence selected from SEQ ID NO: 2, 3, 4, 5, or 6 to a solution containing hemin, wherein the isolated amino acid sequence is effective for forming one or more chemical bonds with hemin. In this embodiment, suitable solutions include in vitro and in vivo solutions such as in vitro or in vivo blood solutions, plasma solutions, or hemin containing solutions, for example.

According to yet another embodiment of the invention, a method of treating a hemorrhagic injury comprises administering a composition comprising at least one isolated amino acid sequence selected from SEQ ID NO: 2, 3, 4, 5, or 6 to a solution containing hemin, wherein the isolated amino acid sequence is effective for forming one or more chemical bonds with hemin.

In certain embodiments of the invention the N-terminus of the amino acid sequence that is administered is acetylated and the C-terminus of the amino acid sequence that is administered is amidated. This is particularly advantageous for stabilizing the amino acid sequences when they are isolated. Acetylation and amidation of the amino acid sequences may be achieved using conventional biochemical techniques.

The inventor unexpectedly discovered that the number of hemin molecules bound by the amino acid sequence administered is a function of the pH. During stroke or stroke-like conditions, the plasma pH decreases from the normal physiological pH of about 7.4. Advantageously, the inventor found that, in some embodiments of the invention, the binding capacity of the amino acid sequence administered for hemin actually increases as the pH decreases. Accordingly, some of the amino acid sequences administered may serve as high-capacity hemin binders during stroke or stroke-like conditions, or any bleeding events that result in release of toxic levels of hemin. Accordingly, other embodiments of the invention may include administering the isolated amino acid sequence when the solution that contains hemin, has a pH below 7.4.

In certain embodiments of the invention, the methods are modified in such a way that the isolated amino acid sequence in the composition consists of SEQ ID NO: 2, 3, 4, 5, or 6. In certain other embodiments, the composition comprises a combination of the isolated amino acid sequences and at least one of isolated amino acid sequences in the composition consists of SEQ ID NO: 2, 3, 4, 5, or 6.

EXAMPLES

This section provides certain examples of aspects of the invention. These examples are not intended to limit the scope of the invention in any way.

Example 1

Peptide and Hemin Sample Preparation

For the following experiments, samples of the SEQ ID NOs: 2, 3, 4, and 6 were purchased commercially. The N-terminus of each peptide was acetylated and the C-terminus of each peptide was amidated to enhance stability. The peptides were prepared in the lyophilized form and stored in a desiccator at −20° C.

The peptides were re-suspended in either 10 mM sodium phosphate buffer, 1 mM EDTA, pH 5.0 or phosphate buffer saline (PBS), pH 7.4. Peptide solutions were then filtered using a 0.22 μm syringe filter to remove any particulates. Peptide concentrations were determined using UV/Vis spectroscopy and the Lambert-Beer law (Cary 300 instrument, Varian/Agilent) using respective extinction coefficients and absorbance values at a wavelength of 280 nm. Specifically, $\Sigma_{280}$ (SEQ ID NO: 2)=5,500 $M^{-1}cm^{-1}$, $\Sigma_{280}$ (SEQ ID NO: 3)=11,000 $M^{-1}cm^{-1}$, $\Sigma_{280}$ (SEQ ID NO: 4)=16,500 $M^{-1}cm^{-1}$, and $\Sigma_{280}$ (SEQ ID NO: 6)=22,000 $M^{-1}cm^{-1}$.

Hemin was dissolved in anhydrous dimethyl sulfoxide (DMSO), and its concentration was determined using extinction coefficient of 174,000 $M^{-1}$ $cm^{-1}$ at 405 nm.

Example 2

Evaluation of PrP$^C$/Hemin Binding Using Fluorescence Spectroscopy

PrP$^C$/hemin binding was evaluated via fluorescence spectroscopy experiments. Fluorescence data were collected using a Cary Eclipse spectrophotometer (Varian/Agilent) at 25° C. and an excitation wavelength of 295 nm. The emission spectrum spanned the 305-450 nm tryptophan fluorescence region. A hemin stock solution at 1 mM concentration was added incrementally into a solution containing SEQ ID NOs: 2, 3, 4, or 6. The starting concentration for SEQ ID NOs: 2, 3, 4, or 6 was about 5-20 μM. A fluorescence spectrum was collected after each hemin addition. Each titration curve was corrected by subtracting a corresponding baseline obtained by titrating hemin incrementally into a buffer devoid of the peptide. Binding calculations indicate that each of the peptides tested binds to hemin on a micromolar level.

Figure 4:
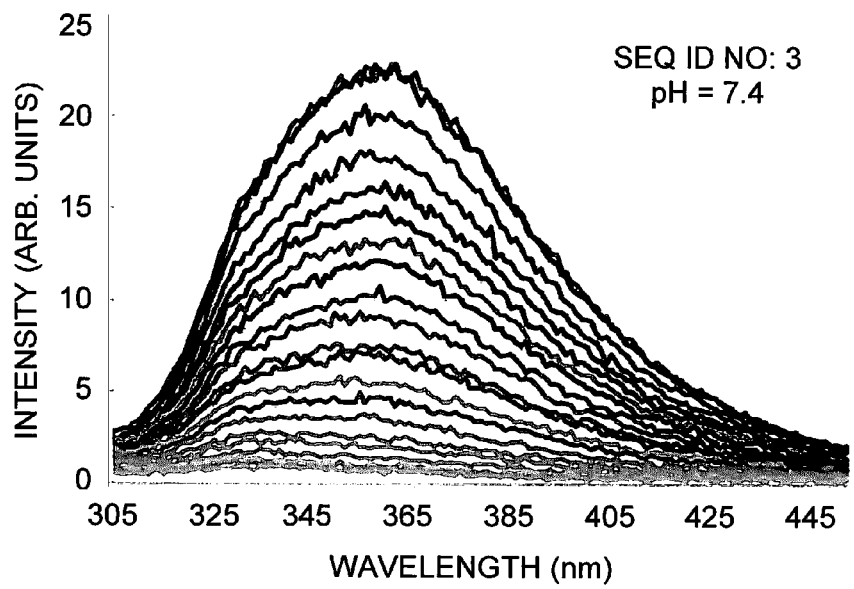
FIG. 4 is graph showing how the fluorescence intensity of SEQ ID NO: 3 at pH=7.4 decreases as hemin is titrated into the solution, thereby indicating binding of hemin to SEQ ID NO: 3.
Figure 5:
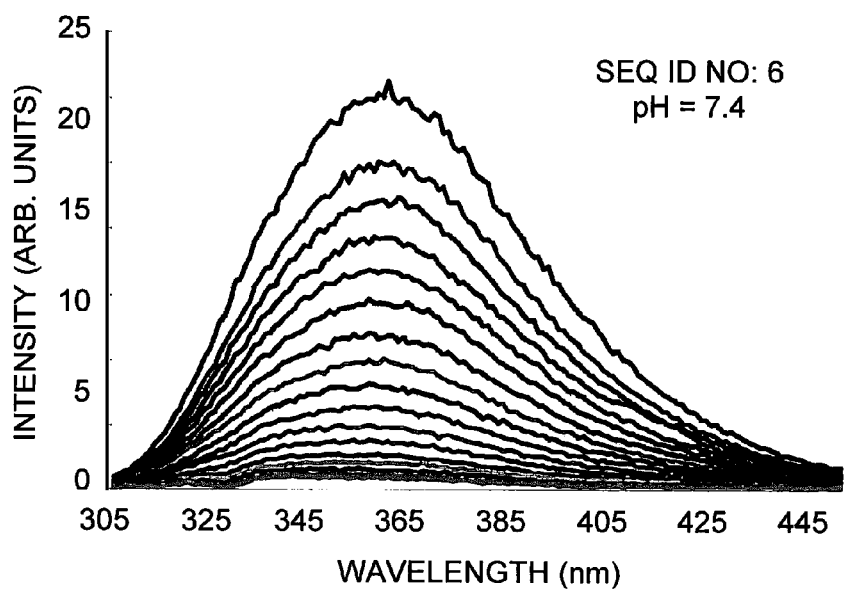
FIG. 5 is graph showing how the fluorescence intensity of SEQ ID NO: 6 at pH=7.4 decreases as hemin is titrated into the solution, thereby indicating binding of hemin to SEQ ID NO: 6.

In a first set of experiments, the fluorescence intensity was recorded as hemin was titrated into a solution containing SEQ ID NO: 3 as shown in FIG. 4 and SEQ ID NO: 6 as shown in FIG. 5. The pH of the solution was 7.4 to simulate normal physiological conditions. The data show that, as hemin is added, the fluorescence intensity decreases. This indicates that hemin forms a chemical bond with SEQ ID NOs: 3 and 6. Similar data for SEQ ID NOs: 2, 4, and 5 were also obtained.

Experiments were also performed at different pH to determine whether SEQ ID NOs: 2, 3, 4, and 6 would bind to hemin with different affinities. In these experiments, pH=7.4 was chosen to simulate normal physiological conditions and pH=5.0 was chosen to simulate stroke conditions.

Figure 6:
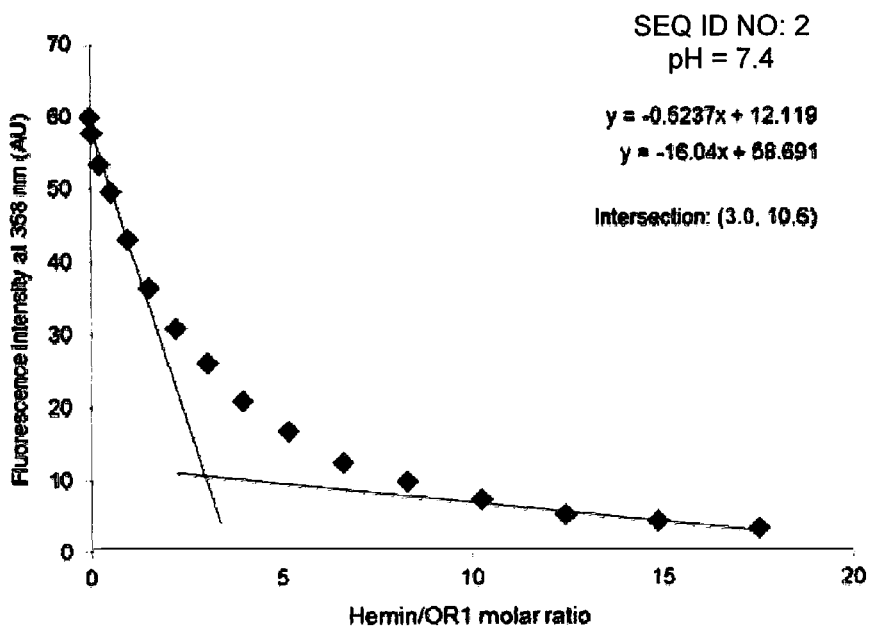
FIG. 6 is a graph of fluorescence intensity of SEQ ID NO: 2 at pH=7.4 where the straight lines indicate fits to the linear equations shown.
Figure 7:
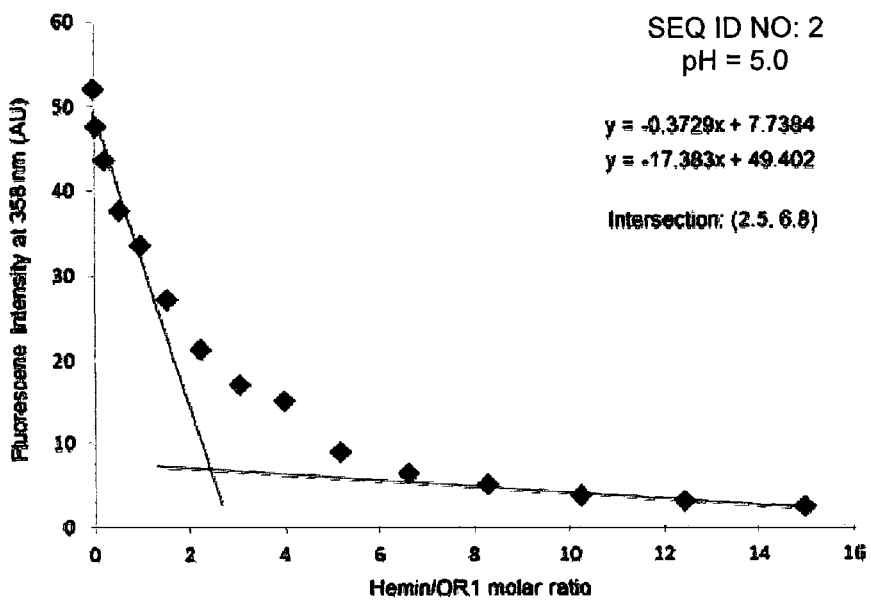
FIG. 7 is a graph of fluorescence intensity of SEQ ID NO: 2 at pH=5.0 where the straight lines indicate fits to the linear equations shown.
Figure 8:
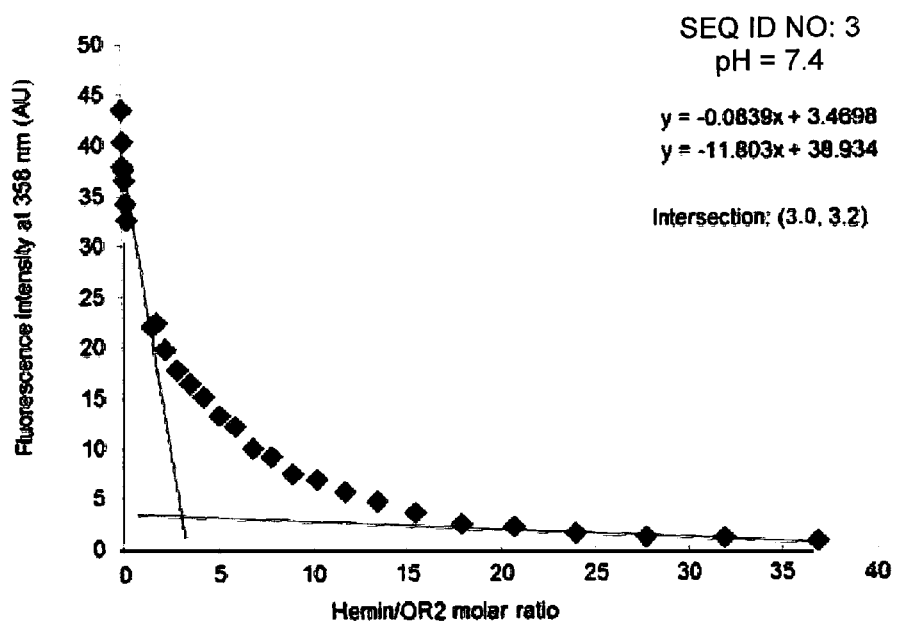
FIG. 8 is a graph of fluorescence intensity of SEQ ID NO: 3 at pH=7.4 where the straight lines indicate fits to the linear equations shown.
Figure 9:
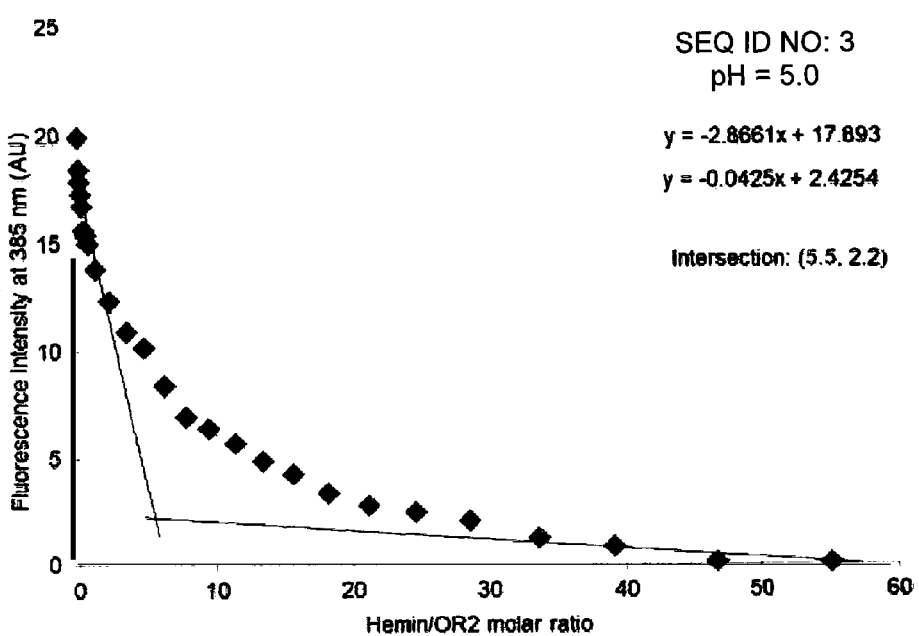
FIG. 9 is a graph of fluorescence intensity of SEQ ID NO: 3 at pH=5.0 where the straight lines indicate fits to the linear equations shown.
Figure 10:
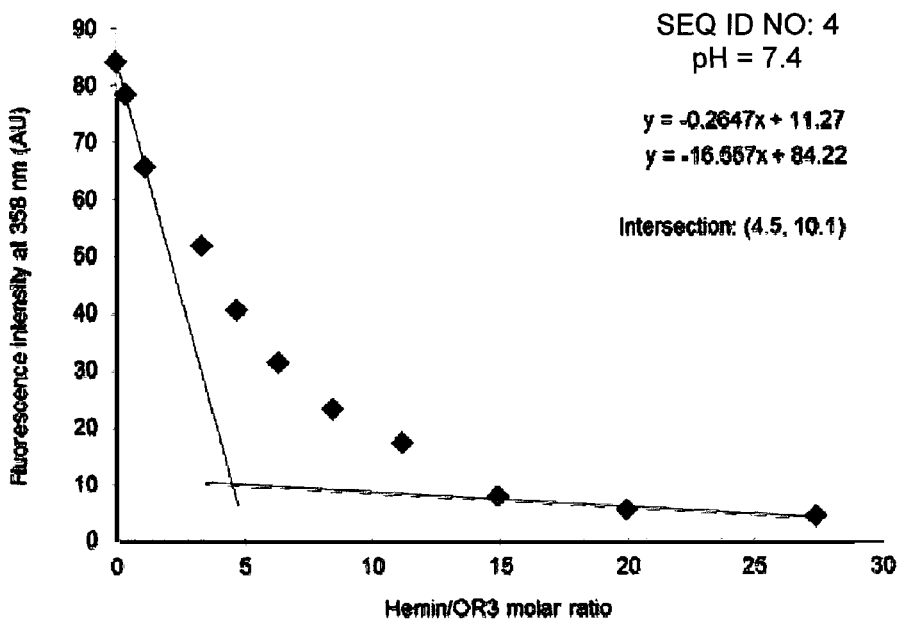
FIG. 10 is a graph of fluorescence intensity of SEQ ID NO: 4 at pH=7.4 where the straight lines indicate fits to the linear equations shown.
Figure 11:
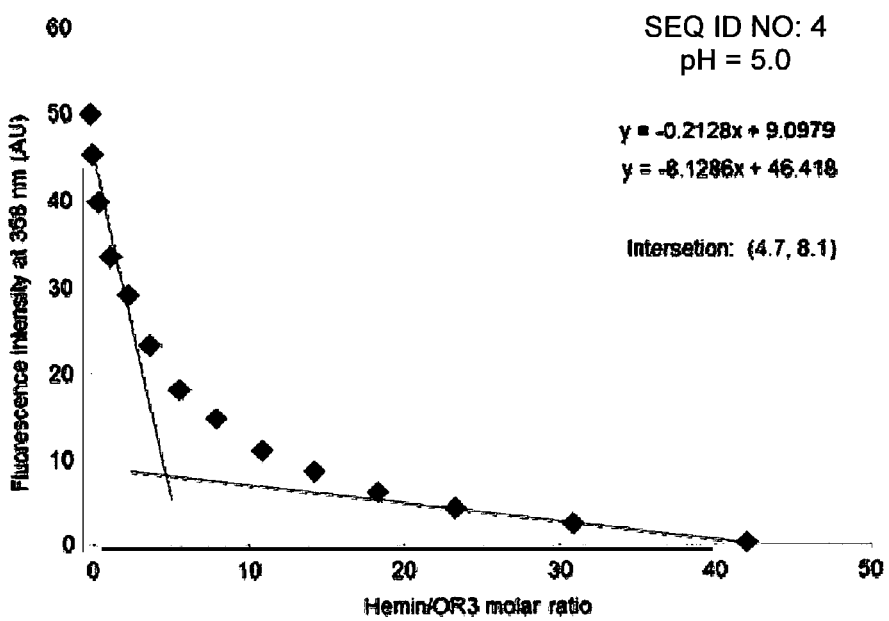
FIG. 11 is a graph of fluorescence intensity of SEQ ID NO: 4 at pH=5.0 where the straight lines indicate fits to the linear equations shown.
Figure 12:
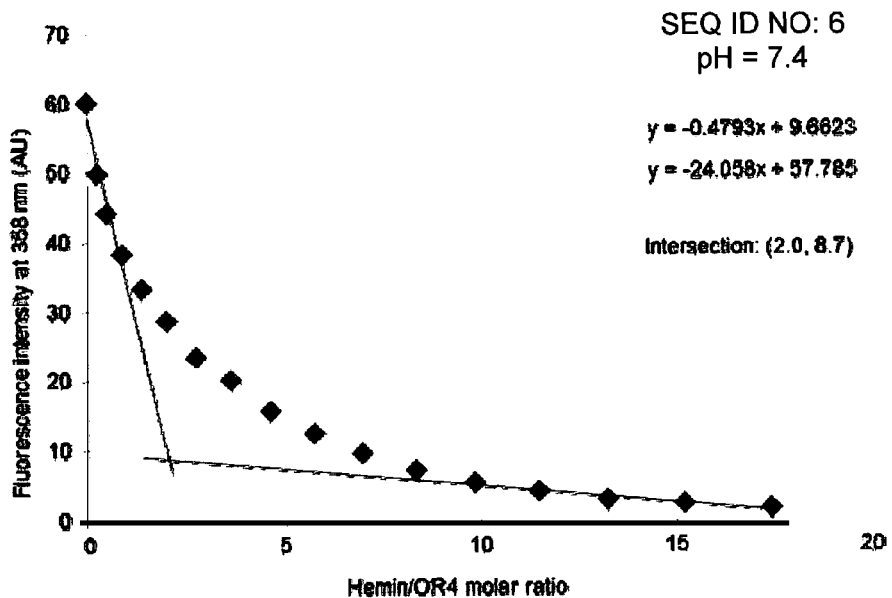
FIG. 12 is a graph of fluorescence intensity of SEQ ID NO: 6 at pH=7.4 where the straight lines indicate fits to the linear equations shown.
Figure 13:
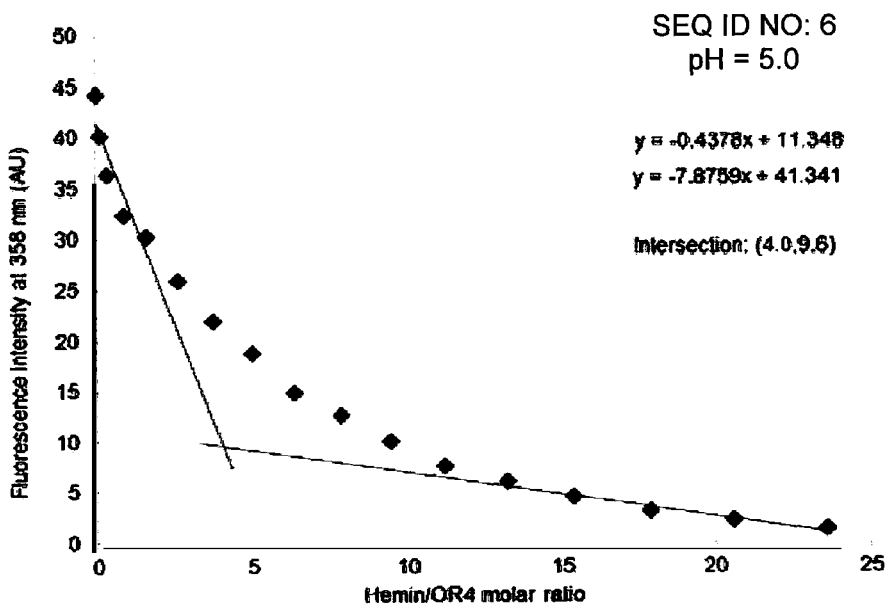
FIG. 13 is a graph of fluorescence intensity of SEQ ID NO: 6 at pH=5.0 where the straight lines indicate fits to the linear equations shown.

FIGS. 6 and 7 show the fluorescence intensity of SEQ ID NO: 2 as hemin was added at a pH of 7.4 and 5.0, respectively. FIGS. 8 and 9 show the fluorescence intensity of SEQ ID NO: 3 as hemin was added at a pH of 7.4 and 5.0, respectively. FIGS. 10 and 11 show the fluorescence intensity of SEQ ID NO: 4 as hemin was added at a pH of 7.4 and 5.0, respectively. FIGS. 12 and 13 show the fluorescence intensity of SEQ ID NO: 6 as hemin was added at a pH of 7.4 and 5.0, respectively.

The solid lines drawn through the data in FIGS. 6-13 are trend fits to the linear parts of the curve. Line fitting was performed using an algorithm Microsoft Excel. The corresponding equation for each linear fit is shown. The x-coordinate of the point at which the two lines intersect was used to estimate the number of hemin molecules bound at pH=7.4 and 5.0. The estimated number of hemin molecules bound to the respective peptide at pH=7.4 and pH=5.0 is presented in TABLE 3.

TABLE 3

| pH dependence of the estimated number of hemin molecules bound to the respective peptide | | |
|---|---|---|
| SEQ ID NO: | pH = 7.4 | pH = 5.0 |
| 2 | 3.0 | 2.5 |
| 3 | 3.0 | 5.5 |
| 4 | 4.5 | 4.7 |
| 6 | 2.0 | 4.0 |

These data indicate that each of SEQ ID NOs: 2, 3, 4, and 6 bind to hemin. Remarkably, they also provide the unexpected result that, at least for SEQ ID NOs: 3, 4, and 6, the binding capacity of the peptide increases with decreasing pH. Thus, these peptides may find use as high-hemin binding capacity agents in methods of the invention.

Example 3

Determination of Whether Octarepeat Peptides are Amyloidogenic

Because PrP$^{SC}$ is linked to the formation of amyloid fibrils that form, for example, in a patient with Alzheimer's disease, control experiments were also performed to determine whether isolated peptides of the octarepeat region could results in amyloid fibril formation as well.

Figure 14:
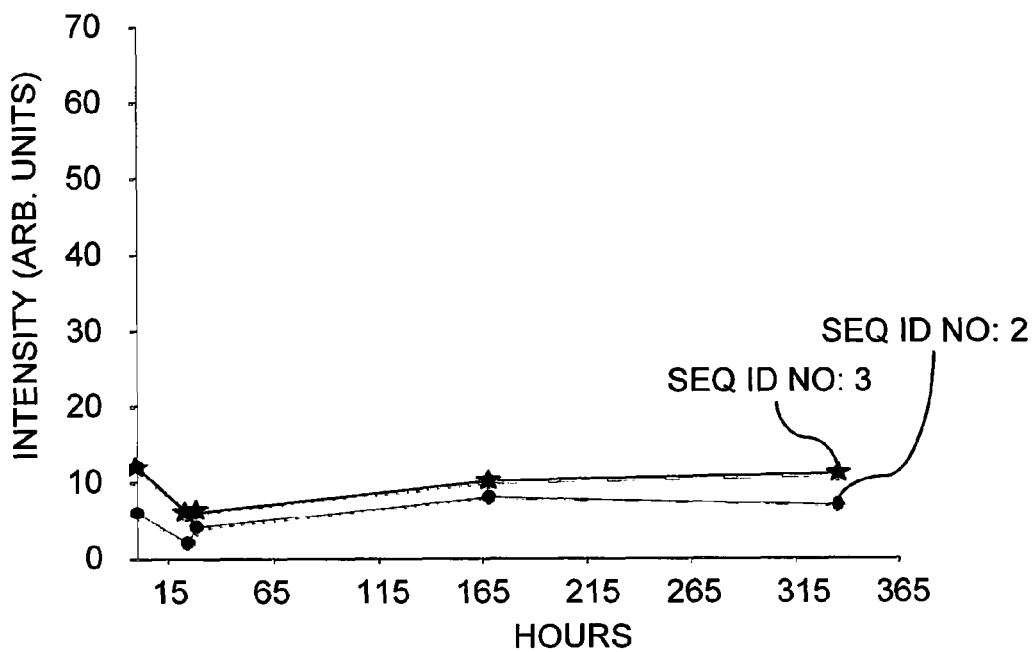
FIG. 14 is a graph of the time dependence of the fluorescence intensity of SEQ ID NOS 2 and 3 stained with 10 µM Thioflavin T and incubated at 37° C. for the time shown.

In order to determine whether the isolated peptide can aggregate and form amyloid fibers, 10 μM of a fluorescent dye used to stain fibers, namely thioflavin T, was added to separate 50 μM samples of SEQ ID NOs: 2 and 3. The fluorescence intensity over the course of about 2 weeks was recorded while the solutions were incubated at 37° C. The results shown in FIG. 14 indicate that that fluorescence intensity remains relatively constant over that time period.

Figure 15:
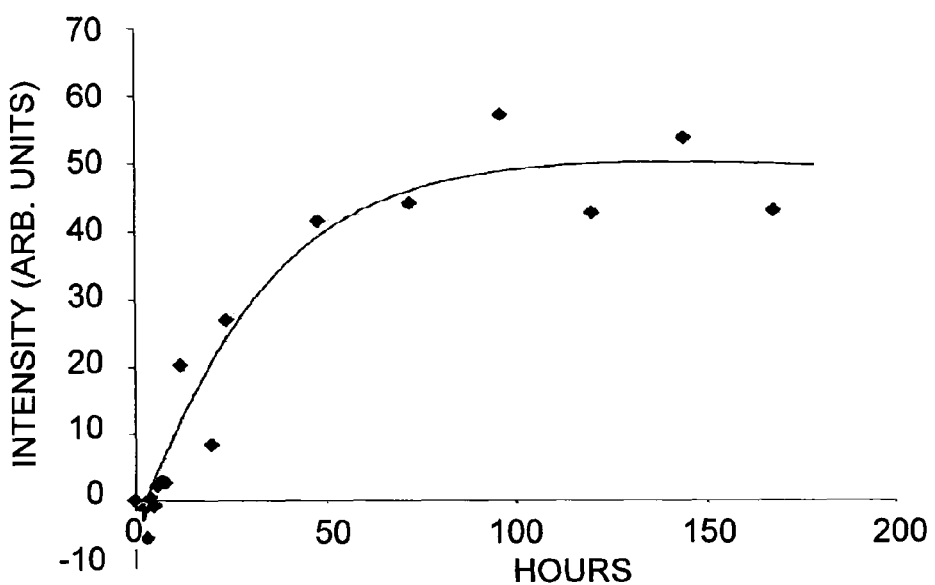
FIG. 15 is a graph of the time dependence fluorescence intensity of the amyloid β peptide under the same experimental conditions as in FIG. 14.

As a comparison, 10 μM of thioflavin T was also used to stain the Alzheimer's amyloid β peptide, which is known to readily form fibers. The resulting data are provided in FIG. 15. The significant rise in the fluorescence intensity signal indicates that fibers were formed. The results indicate that SEQ ID NOs: 2 and 3 and, most likely, SEQ ID NOs 4-6 are not amyloidogenic. This is particularly advantageous as it is desirable avoid administering amyloidogenic substances to patients.

Example 4

Evaluation of PrP$^C$/Hemin Binding Using Surface Plasmon Resonance

PrP$^C$/hemin binding was also evaluated via surface plasmon resonance ("SPR") experiments. SPR data were collected using a Biacore T200 instrument (Biacore/GE_Healthcare). The peptide of interest (SEQ ID NOs: 3, or 6) was immobilized on a CM5 chip using amine coupling chemistry at a surface density of approximately 300 RU. Briefly, this process involved: (1) surface chip activation with a 1:1 ratio of EDS/NHS (0.4 M 1-ethyl-3-(3-dimethylaminopropyl)-carboimide and 0.1M N-hydroxysuccinimide), (2) immobilization of the peptide, and (3) chip surface deactivation with 1M ethanolamine-HCl pH 8.5. A hemin stock solution was prepared in anhydrous dimethyl sulfoxide (DMSO), followed by dilution into the SPR running buffer (HBS-EP+; 10 mM HEPES, 150 mM NaCl, 3 mM EDTA, 0.05% v/v Surfactant P20). Kinetics data were collected using standard Biacore protocols at varying hemin concentrations (3-100 μM). The final concentration of DMSO in the running buffer and hemin samples was 1%.

Figures 16, 17:
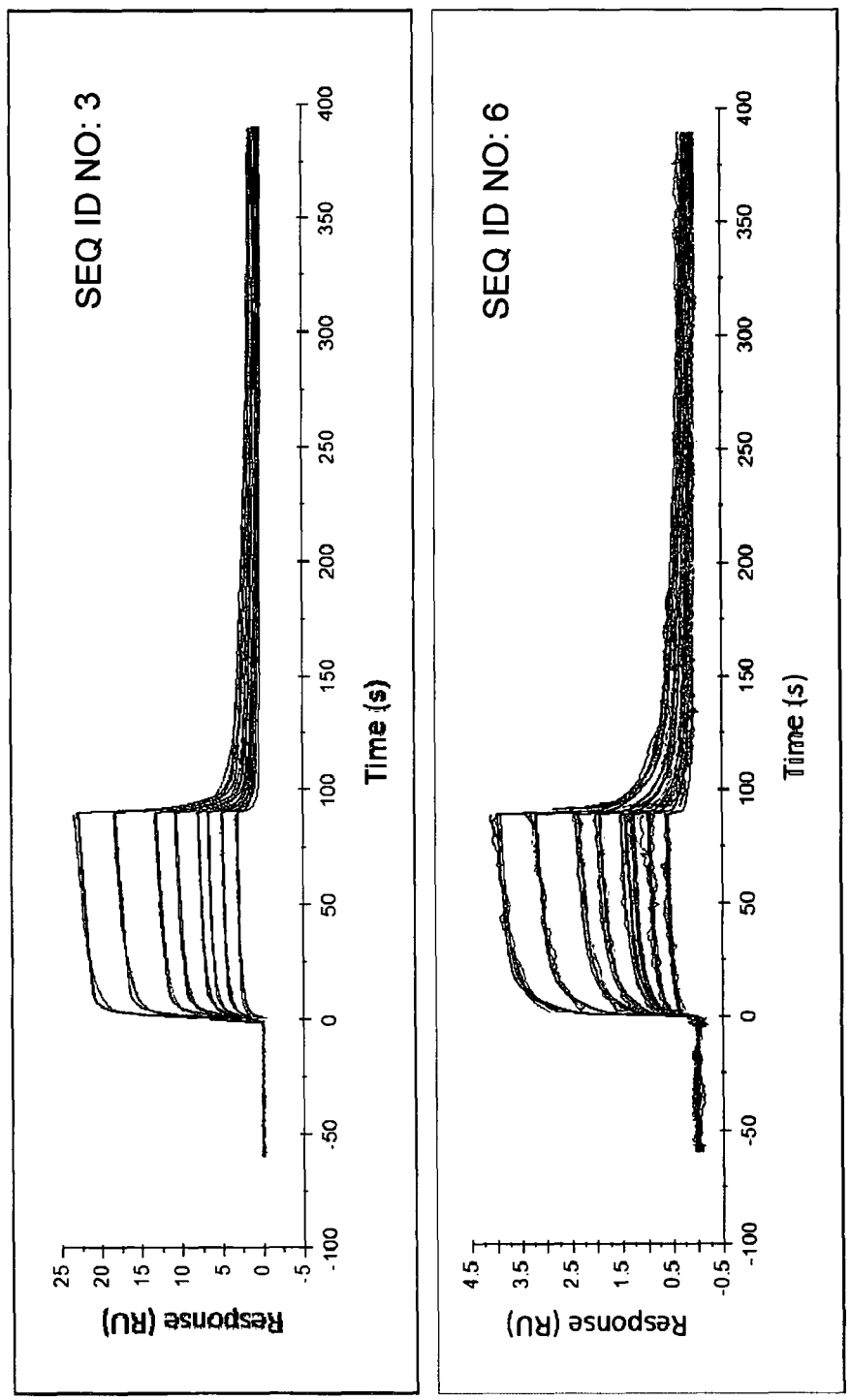
FIG. 16 is a graph of the surface plasmon resonance of SEQ ID NO: 3.
FIG. 17 is a graph of the surface plasmon resonance of SEQ ID NO: 6.

FIGS. 16 and 17 show the SPR response intensity for chips on which SEQ ID NO: 3 and 6 were immobilized as different concentrations of hemin were passed over the chip. As the concentration of hemin increased, the SPR response also increased, indicating that hemin binds to the respective peptide.

Example 5

Determination of the Secondary Structure of the OR Region

Figure 18:
FIG. 18 is a diagram of the structure of the octarepeat region.

Referring to FIG. 18 a three-dimensional structure of the octarepeat region is shown. This structure was obtained from Taubner, et al, "Structure of the Flexible Amino-Terminal Domain of Prion Protein Bound to a Sulfated Glycan," J. Mol. Biol., 395, 475-490 (2010).

Interestingly, the structure includes a β-turn like conformation. Although not intending to be limited to or be bound by theory, it is hypothesized that that the β-turn like conformation may serve as a hemin recognition site.

In order to determine whether the β-turn like secondary structure is conserved in SEQ ID NOs: 2, 3, 4, and 6, the circular dichroism ("CD") spectrum of these sequences was measured and compared to the CD spectrum of a peptide containing residues 23-106 of SEQ ID NO: 1. The peptide containing residues 23-106 of SEQ ID NO: 1 was prepared using bacterial overexpression and subsequent purification. These CD experiments were performed on a Jasco J-810 Spectropolarimeter.

Figure 19:
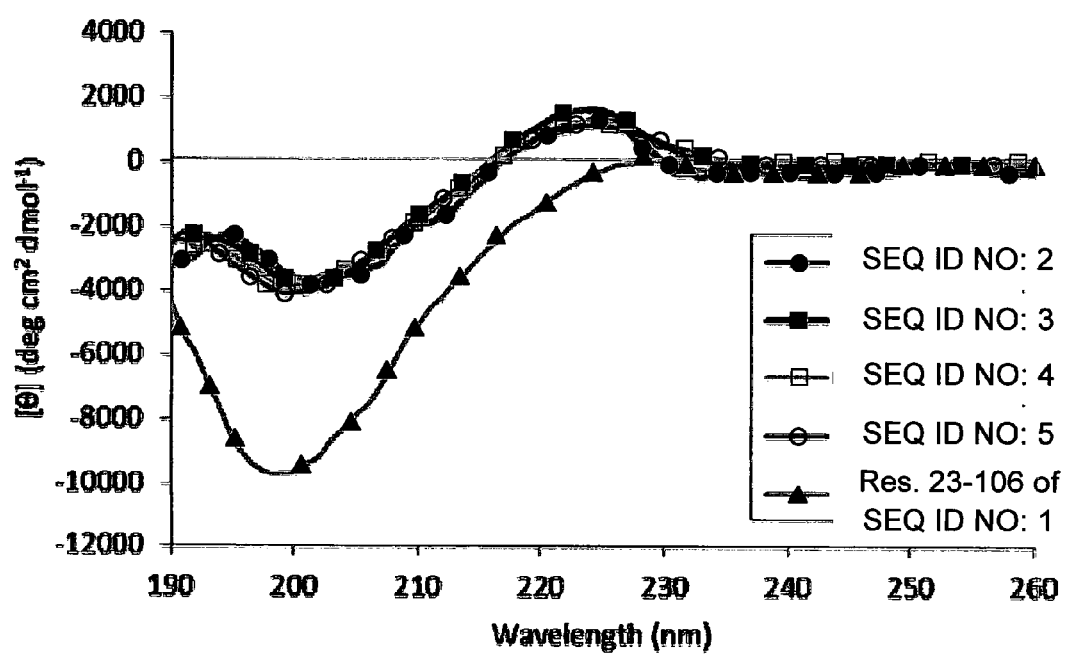
FIG. 19 is a graph of circular dichroism spectroscopy data for SEQ ID NOs: 2, 3, 4, 6 and a peptide containing residues 23-106 of SEQ ID NO: 1.

The results shown in FIG. 19 indicate a significant amount overlap between the CD spectra for each peptide sequence, suggesting that the secondary structure of the octarepeat region is modular and is substantially independent of the number of times the octarepeat sequence is repeated.

Example 6

Crystal Growth and Characterization of Hemin Bound to SEQ ID NO: 3

Figure 20:
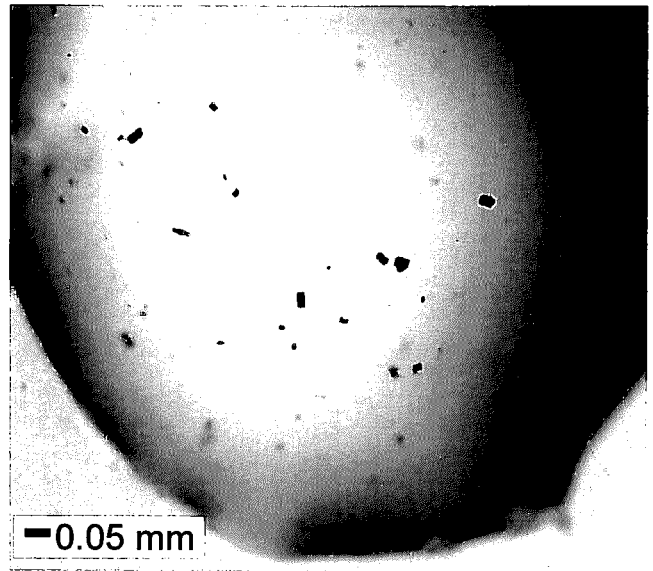
FIG. 20 is a photograph of crystals made of hemin bound to SEQ ID NO: 3.

Crystals of hemin bound to SEQ ID NO: 3 were grown using a conventional hanging drop vapor diffusion method with a starting SEQ ID NO: 3 concentration of 10 mg/mL and a hemin/SEQ ID NO: 3 ratio of 3:1. Crystals were observed after microseeding a parent crystal, which was obtained after screening various Hampton crystal solutions. A photograph of exemplary crystals suspended in a drop is shown in FIG. 20.

Figure 21:
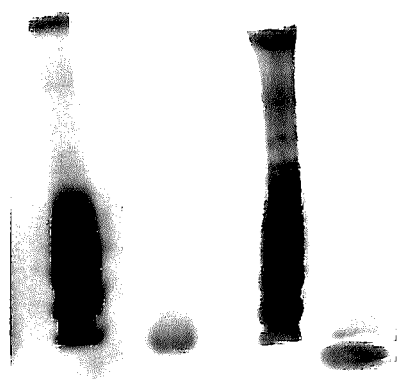
FIG. 21 shows a comparison of gel electrophoresis data for SEQ ID NO: 3 eluted from the crystal (left panel) and SEQ ID NO: 3 used as a control.

The composition of the crystals was evaluated using gel electrophoresis and Izit dye. The left panel of FIG. 21 shows the result of such a gel electrophoresis experiment on the SEQ ID NO: 3 eluted from the hemin/SEQ ID NO: 3 crystals. The right panel of FIG. 21 shows the result of a similar gel electrophoresis experiment of the lyophilized SEQ ID NO: 3 in the absence of hemin used as a control. By comparing the two panels, it is clear that the hemin/SEQ ID NO: 3 crystals contain SEQ ID NO: 3. As the crystals are colored, it is clear that they also contain hemin.

Figure 22:
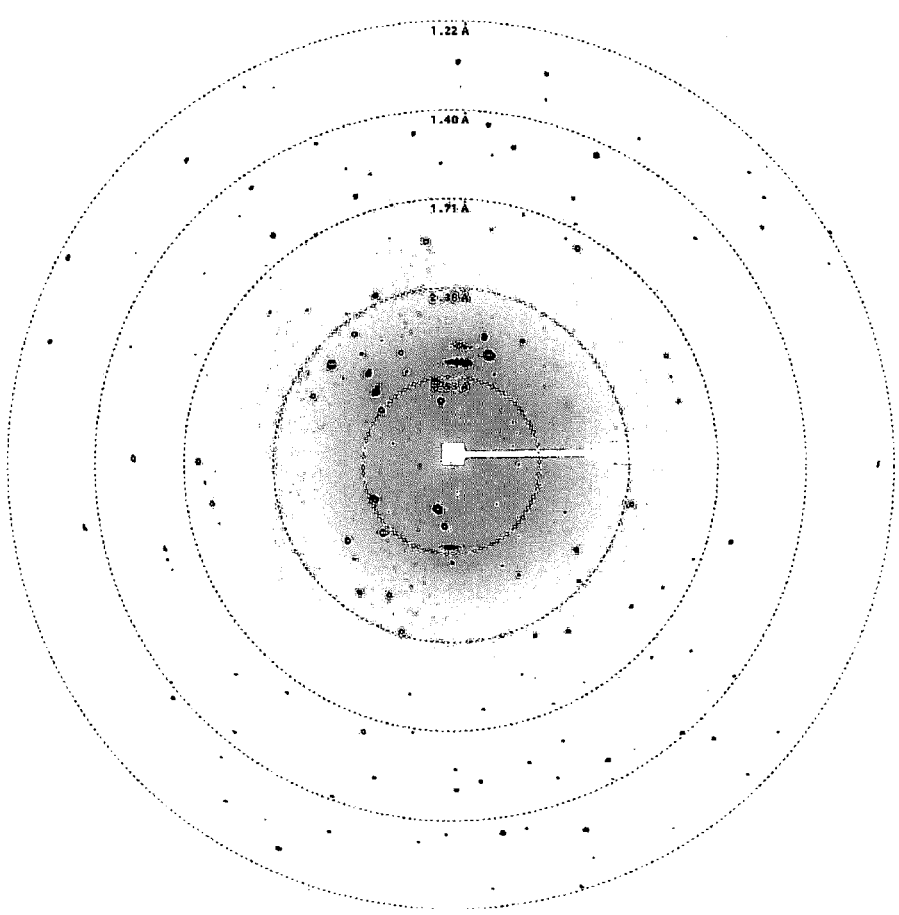
FIG. 22 shows an X-ray diffraction pattern taken from one of the crystals.

In order to prove that samples were indeed crystalline and not just amorphous solids, X-ray diffraction data were collected. FIG. 22 shows a clear X-ray diffraction pattern taken from one of the crystals. The fact that a clear diffraction pattern was obtained, unambiguously proves that the SEQ ID NOs: 2, 3, 4, 5, and 6 are capable of binding hemin. Further experiments are underway to determine the crystal structure of this complex, which will provide additional details as to how the hemin-peptide interaction occurs.

Example 7

Treatment of Rats Following Traumatic Brain Injury

This example shows that a condition characterized by cellularly toxic hemin levels, such as a hemorrhagic injury, can be treated with portions of the N-terminal domain of PrP$^C$ by binding hemin.

Nine rats were equally divided into three test groups: a vehicle test group, a treated test group, and a control test group. The three rats in the vehicle test group were subjected to a traumatic brain injury that caused hemorrhaging and were not treated with a portion of the N-terminal domain of PrP$^C$. The three rats in the treated test group were subjected to the same brain injury and were treated interperitoneally with a 8 mg/kg dose of SEQ ID NO: 3 at 1 and 6 hours post-injury. The three rats in the control test group were not injured or treated.

We used an established traumatic/hemorrhagic brain injury rat animal model to test the efficacy of selected peptides at alleviating brain tissue damage due to bleeding and release of hemin. Mice were anesthetized with isoflurane and the skull was shaved and aseptically prepped and fitted to a stereotaxic device. A midline incision was performed and the periosteum was retracted. A 3 mm circular piece of skull was removed above the medial frontal cortex (MFC) leaving the dura intact. A piston was placed on the dura. The piston was then used at a velocity of 3.5 m/sec to produce a contusion at a depth of 2 mm for moderate injury. Following injury, the cranium was closed with cranioplast and tissue closed with silk suture. Topical analgesics were applied. This procedure is routinely performed by most investigators conducting work on traumatic brain injury and represents one of the most consistent and reproducible forms of injury. See Hoffman, S. W., et al., *Journal of Neurotrauma*, Vol. 11(4), pp. 417-431, (1994) and VanLandingham, J. W., et al., *Neuropharmacology*, Vol. 51 (6), pp. 1078-1085 (2006).

Brain edema was measured 24 hours after the injury as described by Liu et al in *Experimental & Translational Stroke Medicine*, Vol. 4:12 (2012). The portions of this article that describe measuring brain edema are incorporated by reference. Each rat's brain was quickly removed after the rat was euthanized. Brain tissue from the impacted region was collected using punch biopsy. The brain's wet weight was initially measured. Subsequently, the brain's dry weight was determined after heating the tissue for three hours in a speed-vacuum device. Water content was calculated as % H2O=(1−dry weight/wet weight)×100%.

Figure 23:
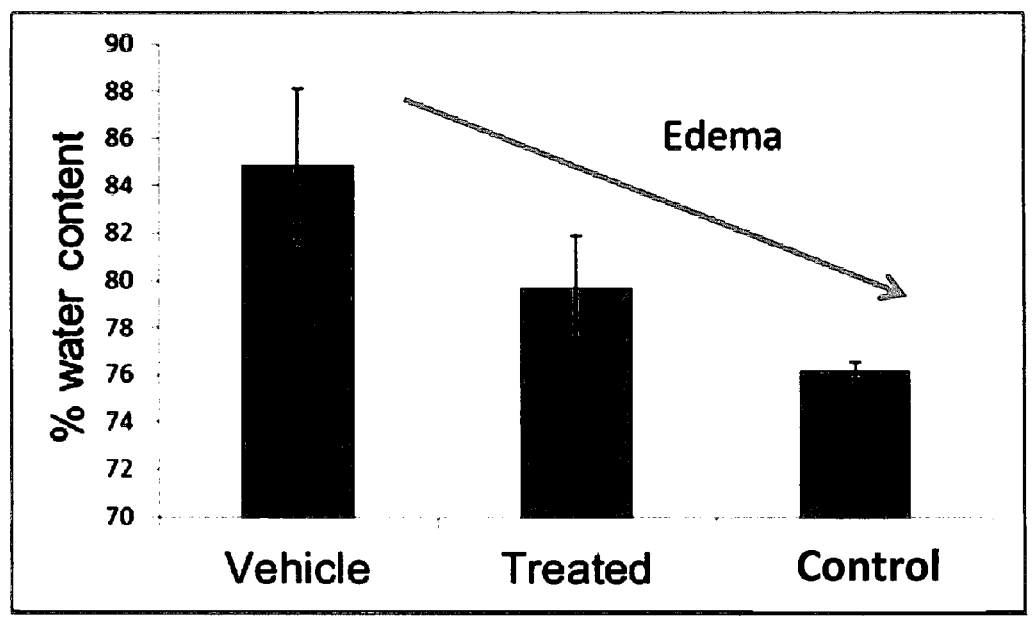
FIG. 23 is a bar graph comparing the % water content in rat brains without injury but without treatment (vehicle), with injury and treatment (treated), and without injury or treatment).

The brain edema test results are summarized in TABLE 4 and FIG. 23 in terms of % water content. The data confirm that the injury caused significant amount of brain swelling relative to the control group. Significantly, the data also confirm that SEQ ID NO: 3 reduced the brain swelling in the treated rats.

These data show that portions of the N-terminal domain of the octarepeat peptide successfully treat a condition characterized by cellularly toxic hemin levels, such as a hemorrhagic injury. The reduction in swelling indicates that binding hemin using SEQ ID NO: 3 subsequent to such an injury can alleviate some of the damaging effects of the injury.

TABLE 4

Rat test results

| SAMPLE # | VEHICLE | TREATED | CONTROL |
|---|---|---|---|
| 1 | 88.62 | 80.93 | 76.56 |
| 2 | 83.37 | 77.24 | 76.12 |
| 3 | 82.61 | 80.98 | 75.86 |
| Average | 84.87 | 79.72 | 76.18 |
| Std. dev. | 3.27 | 2.14 | 0.35 |

The invention has been described above with reference to the accompanying drawings, in which preferred embodiments of the invention are shown. Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described. The skilled should understand that the methods and materials used and described are examples and may not be the only ones suitable for use in the invention.

In the specification set forth above there have been disclosed typical preferred embodiments of the invention, and although specific terms are employed, the terms are used in a descriptive sense only and not for purposes of limitation. The invention has been described in some detail, but it will be apparent that various modifications and changes can be made within the spirit and scope of the invention as described in the foregoing specification and as defined in the appended claims.

That which is claimed is:

1. A method of treating a condition characterized by cellularly toxic hemin levels, the method comprising administering a composition comprising an isolated amino acid sequence selected from the group consisting of SEQ ID NOs: 2, 3, 4, 5, 6, and combinations thereof to a subject identified as having a condition characterized by cellularly toxic hemin levels.

2. The method of claim 1, wherein the composition comprises a combination of the isolated amino acid sequences and at least one of the isolated amino acid sequences in the composition consists of SEQ ID NO: 2.

3. The method of claim 1, wherein the composition comprises a combination of the isolated amino acid sequences and at least one of the isolated amino acid sequences in the composition consists of SEQ ID NO: 3.

4. The method of claim 1, wherein the composition comprises a combination of the isolated amino acid sequences and at least one of the isolated amino acid sequences in the composition consists of SEQ ID NO: 4.

5. The method of claim 1, wherein the composition comprises a combination of the isolated amino acid sequences and at least one of the isolated amino acid sequences in the composition consists of SEQ ID NO: 5.

6. The method of claim 1, wherein the composition comprises a combination of the isolated amino acid sequences and at least one of the isolated amino acid sequences in the composition consists of SEQ ID NO: 6.

7. The method of claim 1, wherein the N-terminus of the isolated amino acid sequence is acetylated and the C-terminus of the isolated amino acid sequence is amidated.

8. A method of treating a condition characterized by cellularly toxic hemin levels, the method comprising administering a composition comprising at least one isolated amino acid sequence consisting essentially of SEQ ID NO: 2, 3, 4, 5, or 6 to a subject identified as having a condition characterized by cellularly toxic hemin levels.

9. The method of claim 8, wherein the isolated amino acid sequence consists of SEQ ID NO: 2.

10. The method of claim 8, wherein the isolated amino acid sequence consists of SEQ ID NO: 3.

11. The method of claim 8, wherein the isolated amino acid sequence consists of SEQ ID NO: 4.

12. The method of claim 8, wherein the isolated amino acid sequence consists of SEQ ID NO: 5.

13. The method of claim 8, wherein the isolated amino acid sequence consists of SEQ ID NO: 6.

14. The method of claim 8, wherein the N-terminus of the isolated amino acid sequence is acetylated and the C-terminus of the isolated amino acid sequence is amidated.

15. A method of treating a hemorrhagic injury, the method comprising administering a composition comprising at least one isolated amino acid sequence selected from SEQ ID NO: 2, 3, 4, 5, or 6 to a subject identified as having a hemmorhagic injury, wherein the isolated amino acid sequence is effective for forming one or more chemical bonds with hemin.

16. The method of claim 15, wherein the composition comprises a combination of the isolated amino acid sequences and at least one of the isolated amino acid sequences in the composition consists of SEQ ID NO: 2.

17. The method of claim 15, wherein the composition comprises a combination of the isolated amino acid sequences and at least one of the isolated amino acid sequences in the composition consists of SEQ ID NO: 3.

18. The method of claim 15, wherein the composition comprises a combination of the isolated amino acid sequences and at least one of the isolated amino acid sequences in the composition consists of SEQ ID NO: 4.

19. The method of claim 15, wherein the composition comprises a combination of the isolated amino acid sequences and at least one of the isolated amino acid sequences in the composition consists of SEQ ID NO: 5.

20. The method of claim 15, wherein the composition comprises a combination of the isolated amino acid sequences and at least one of the isolated amino acid sequences in the composition consists of SEQ ID NO: 6.

21. The method of claim 15, wherein the N-terminus of the isolated amino acid sequence is acetylated and the C-terminus of the isolated amino acid sequence is amidated.

22. The method of claim 15, wherein the composition is administered when the pH of the subject's plasma is below 7.4.

23. The method of claim 15, wherein the hemorrhagic injury is treated by alleviating edema at the injury site.

* * * * *